(12) United States Patent
Morikoshi

(10) Patent No.: US 12,077,809 B2
(45) Date of Patent: Sep. 3, 2024

(54) FREEZE-DRIED STRUCTURE AND PRODUCING METHOD THEREOF

(71) Applicant: ENPLAS CORPORATION, Kawaguchi (JP)

(72) Inventor: Daisuke Morikoshi, Saitama (JP)

(73) Assignee: ENPLAS CORPORATION, Saitama (JP)

( * ) Notice: Subject to any disclaimer, the term of this patent is extended or adjusted under 35 U.S.C. 154(b) by 621 days.

(21) Appl. No.: 17/241,922

(22) Filed: Apr. 27, 2021

(65) Prior Publication Data

US 2022/0340961 A1    Oct. 27, 2022

(51) Int. Cl.
*C12Q 1/6844* (2018.01)
*F26B 5/06* (2006.01)
*F26B 25/06* (2006.01)

(52) U.S. Cl.
CPC .......... *C12Q 1/6846* (2013.01); *F26B 25/063* (2013.01); *F26B 5/06* (2013.01)

(58) Field of Classification Search
CPC ......... F26B 25/063; F26B 5/06; C12Q 1/6846
USPC .................................... 34/284, 92
See application file for complete search history.

(56) References Cited

U.S. PATENT DOCUMENTS

| | | | |
|---|---|---|---|
| 3,308,552 A * | 3/1967 | Kaufman | F26B 5/06 34/92 |
| 4,197,658 A * | 4/1980 | Fraser | F26B 5/06 34/92 |
| 10,322,182 B2 | 6/2019 | Spira et al. | |
| 10,406,528 B1 * | 9/2019 | Phaneuf | G01N 21/64 |
| 10,543,274 B2 | 1/2020 | Spira et al. | |
| 10,793,327 B2 * | 10/2020 | Weimer | A61J 1/1468 |
| 10,869,928 B2 | 12/2020 | Spira et al. | |
| 11,604,026 B2 * | 3/2023 | Johnson | A01N 1/0263 |
| 2014/0128462 A1 | 5/2014 | Spira et al. | |
| 2017/0049894 A1 | 2/2017 | Spira et al. | |
| 2019/0240332 A1 | 8/2019 | Spira et al. | |
| 2020/0009252 A1 | 1/2020 | Spira et al. | |
| 2020/0121794 A1 | 4/2020 | Spira et al. | |
| 2020/0288703 A1 * | 9/2020 | Parakininkas | A01N 1/0289 |
| 2020/0345848 A1 | 11/2020 | Spira et al. | |
| 2022/0340961 A1 * | 10/2022 | Morikoshi | C12Q 1/686 |
| 2023/0168033 A1 * | 6/2023 | Morikoshi | B01L 3/523 34/284 |

FOREIGN PATENT DOCUMENTS

| | | | | |
|---|---|---|---|---|
| CA | 3130700 A1 * | 9/2020 | ......... | A01N 1/0252 |
| JP | 2014-512402 | 5/2014 | | |
| WO | 2012/146625 | 11/2012 | | |
| WO | WO-2020185909 A3 * | 12/2020 | ......... | A01N 1/0252 |

* cited by examiner

*Primary Examiner* — Stephen M Gravini
(74) *Attorney, Agent, or Firm* — HSML P.C.

(57) ABSTRACT

An object of the present invention is to provide a new freeze-dried article that is easy to handle and a producing method thereof. A freeze-dried structure of the present invention includes a freeze-dried article and a support member, wherein the support member has an embedded region and a protruding region, the embedded region of the support member is embedded in the internal portion of the freeze-dried article, and the protruding region of the support member protrudes outward from the freeze-dried article.

7 Claims, 7 Drawing Sheets

FREEZE-DRIED STRUCTURE AND PRODUCING METHOD THEREOF

BACKGROUND OF THE INVENTION

1. Field of the Invention

The present invention relates to a freeze-dried structure and a producing method thereof.

2. Description of Related Art

Nucleic aid amplification such as PCR is performed in a liquid reaction system. In recent years, a freeze-dried reagent, in which all of necessary reagents are mixed, is used as the reagent for such amplification from the viewpoint of stability, convenience, and the like. The freeze-dried reagent can be produced, for example, by preparing a reagent liquid in which a plurality of reagents are mixed, introducing the reagent liquid into an internal portion of a chamber, and performing freeze drying treatment.

However, a freeze-dried material is brittle, and thus the obtained freeze-dried reagent may be chipped or broken when it is held by a holding tool such as tweezers having a holding portion. Specifically, such damage occurs, for example, when the freeze-dried reagent is taken out from the internal portion of the chamber or when the freeze-dried reagent is introduced into a nucleic acid amplification reaction system. These issues regarding the handling of freeze-dried materials are not limited to the above-mentioned reagent, and, for example, the same applies to food items, cosmetics, and the like.

SUMMARY OF THE INVENTION

Thus, it is an object of the present invention to provide a new freeze-dried article that is easy to handle and a producing method thereof.

The present invention is directed to a freeze-dried structure including a freeze-dried article and a support member,
  wherein the support member has an embedded region and a protruding region,
  the embedded region of the support member is embedded in an internal portion of the freeze-dried article, and
  the protruding region of the support member protrudes outward from the freeze-dried article.

Furthermore, the present invention is directed to a method for producing a freeze-dried structure, including:
  introducing a support member and a liquid into an internal portion of a chamber; and
  performing freeze drying treatment in the chamber,
  wherein the support member has a main body and a projecting member,
  the main body and the projecting member are connected,
  in the support member, the projecting member projects outward from the main body, from an external face of the main body,
  in the introducing,
    the support member is arranged such that a main body side thereof faces a bottom side of the chamber and a projecting member side thereof faces a side opposite to the bottom of the chamber, and
    the liquid is introduced into the internal portion of the chamber until at least a part of the projecting member of the support member is exposed and an entirety or a part of the main body of the support member is covered, and
  in the freeze drying,
    a freeze-dried structure in which the support member and a freeze-dried article of the liquid are included and the part of the projecting member of the support member protrudes from the freeze-dried article is produced through the freeze drying treatment.

According to the freeze-dried structure of the present invention, the protruding region of the support member protrudes outward from the freeze-dried article. Accordingly, it is possible to hold the protruding region of the freeze-dried structure using a holding tool such as tweezers, without holding the surface of the freeze-dried article. Thus, it is possible to perform handling while reducing damage to a brittle freeze-dried article in the freeze-dried structure.

BRIEF DESCRIPTION OF THE DRAWINGS

FIG. 2A is a cross-sectional view showing an example of a freeze drying treatment vessel, FIG. 2B is a cross-sectional view showing an example of a state in which a support member has been introduced into a chamber of the vessel, FIG. 2C is a cross-sectional view showing an example of a state in which the support member and a liquid have been introduced into the chamber of the vessel, and FIG. 2D is a cross-sectional view showing an example of a state in which the freeze-dried structure is produced through freeze drying treatment performed in the chamber of the vessel.

DETAILED DESCRIPTION OF THE INVENTION

Freeze-Dried Structure

Figure 1:
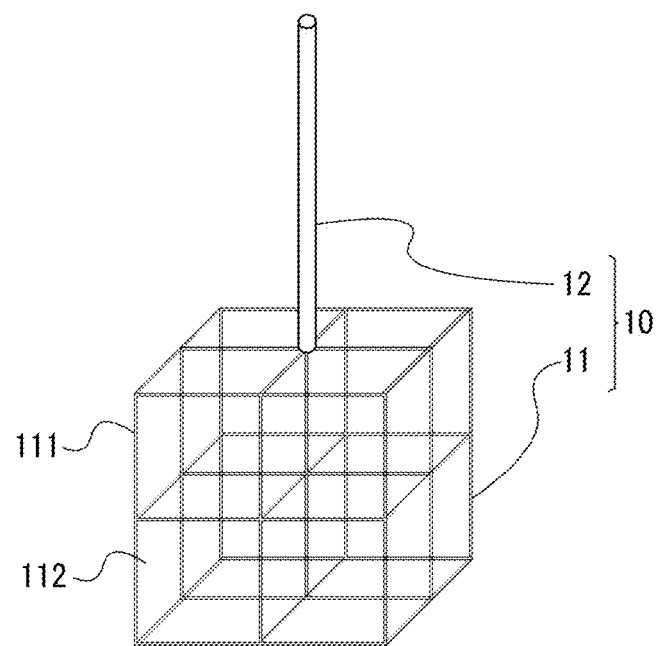
FIG. 1 is a perspective view schematically showing a support member in Embodiment 1.

As described above, a freeze-dried structure of the present invention has a freeze-dried article and a support member, wherein the support member has an embedded region and a protruding region. The embedded region of the support member is embedded in an internal portion of the freeze-dried article, and the protruding region of the support member protrudes outward from the freeze-dried article.

The embedded region of the support member is, for example, a region of the support member positioned closer to the inner side than the external face of the freeze-dried article is, and the protruding region of the support member is, for example, a region protruding outward from the external face of the freeze-dried article.

The freeze-dried structure of the present invention has the freeze-dried article and the support member, and the protruding region of the support member projecting outward from the freeze-dried article can be used as a holdable portion. The holdable portion is, for example, a region that is held by a holding tool such as tweezers during handling of the freeze-dried structure.

The freeze-dried structure of the present invention can be produced, for example, using a later-described method for producing the freeze-dried structure of the present invention. The freeze-dried structure of the present invention can be produced through the freeze drying treatment in a state in which a part of the support member is covered in the liquid, as will be described later, and thus it can be said that a freeze-dried article produced from the liquid through the freeze drying treatment and the support member are integrated. That is to say, in the freeze-dried structure of the present invention, for example, the freeze-dried article and the support member can be said to be an integrated article in which they are in contact with each other at the embedded region of the support member.

The support member may be, for example, a non-porous material or a porous material, or may be constituted by both materials. A non-porous material is, for example, a structure having no void. If the embedded region of the support member is a non-porous material, the freeze-dried article is, for example, in contact with the outer face of the embedded region of the support member and is formed on the outer side of the embedded region. Furthermore, if the embedded region of the support member is a porous material, the freeze-dried article is formed, for example, in voids defining pores in the embedded region and on the outer side of the embedded region.

Furthermore, the embedded region of the support member may also be, for example, a frame structure. If the embedded region of the support member is the frame structure, the freeze-dried article is formed, for example, in a region (void) defined by a frame member constituting the frame structure in the embedded region or on the outer side of the embedded region.

The material of the support member is not particularly limited, and may be, for example, resin, paper, fiber, or the like. Examples of the resin include polypropylene (PP), nylon, polyethylene terephthalate (PET), and polyethylene (PE). Examples of the fiber include a natural fiber and a chemical fiber.

The support member may be, for example, a non-woven fabric or a woven fabric, and the material thereof is not particularly limited, and may be, for example, as described above.

The structure of the support member is not particularly limited, and may be, for example, as described in a later description of the producing method of the present invention.

In the freeze-dried structure of the present invention, the type of freeze-dried article is not particularly limited, and may be, for example, a freeze-dried article of a reagent, a food item, a cosmetic, or the like. The reagent is not particularly limited, and may be, for example, reagents for use in various reactions. In the freeze-dried structure of the present invention, if the freeze-dried article contains a reagent, the reagent may be constituted by, for example, one type of reagent component, two or more types of reagent components, or a mixture of a plurality of reagent components for use in the reactions.

Specific examples of the reagent include a reagent for nucleic acid amplification. The type of nucleic acid amplification is not particularly limited, and may be, for example, a non-isothermal amplification method or an isothermal amplification method. The non-isothermal amplification method is, for example, a method in which the temperature is changed in the processes of separation, annealing, amplification, and the like, and examples thereof include PCR. The isothermal amplification method is, for example, a method in which the processes are performed at a constant temperature, and examples thereof include LAMP. The reagent is not particularly limited, and, for example, known reagents can be used according to the type of nucleic acid amplification. The reagent may be constituted by, for example, one type of reagent component or two or more types of reagent components, but it is preferably a mixture of a plurality of reagent components for use in the nucleic acid amplification. The reagent is not particularly limited, and known reagents can be selected as appropriate according to the type of nucleic acid amplification. Specific examples of the reagent component in the reagent for nucleic acid amplification include a primer, a probe, a monomer nucleic acid (e.g., dNTP), and a polymerase.

The size of the freeze-dried structure of the present invention is not particularly limited. In the freeze-dried structure of the present invention, if the freeze-dried article contains the reagent (e.g., a reagent for nucleic acid amplification as a specific example), the following size can be given as a specific example of the size of the freeze-dried structure of the present invention. Note that the present invention is not limited to these examples.

Overall size (height): 20 mm or less
Sin, of freeze-dried article (height): 10 mm or less
Sin, of protruding region (height): 5 mm or more and 15 mm or less
Ratio (ratio by height) between freeze-dried article and protruding region:freeze-dried article:protruding region=1:9 to 9:1

If the freeze-dried structure of the present invention contains the reagent, for example, it can be used for a reaction that uses the reagent. When performing nucleic acid amplifications, for example, it is possible to cause a nucleic aid amplification reaction to occur by mixing the freeze-dried structure and a sample, further mixing an aqueous solvent as necessary, and performing temperature treatment according to the type of nucleic aid amplification. The aqueous solvent is, for example, water, a buffer solution, or the like.

The type of reaction vessel for performing the nucleic aid amplification is not particularly limited, and may be, for example, a dedicated vessel such as a reaction tube or cartridge (made of resin, etc), and the freeze-dried structure can be, for example, manually or automatically introduced into the internal portion of the reaction vessel During introduction, as described above, it is possible to perform handling while holding a protruding region (a holdable portion) in the support member of the freeze-dried structure.

Method for Producing Freeze-Dried Structure

As described above, the method for producing the freeze-dried structure of the present invention includes; introducing a support member and a liquid into an internal portion of a chamber; and performing freeze drying treatment in the chamber, wherein the support member has a main body and a projecting member, the main body and the projecting member are connected, and, in the support member, the projecting member projects outward from the main body, from an external face of the main body, in the introducing, the support member is arranged such that a main body side thereof faces a bottom side of the chamber and a projecting member side thereof faces a side opposite to the bottom of the chamber, and the liquid is introduced into the internal portion of the chamber until at least a part of the projecting member of the support member is exposed and an entirety or a part of the main body of the support member is covered (immersed), and in the freeze drying, a freeze-dried structure in which the support member and a freeze-dried article of the liquid are included and the part of the projecting member of the support member protrudes from the freeze-dried article is produced through the freeze drying treatment.

The method for producing the freeze-dried structure of the present invention may be as described in the description of the freeze-dried structure of the present invention unless otherwise described. Furthermore, the description of the method for producing the freeze-dried structure of the present invention may apply to the freeze-dried structure of the present invention unless otherwise described.

According to the producing method of the present invention, it is possible to obtain the above-described freeze-dried structure of the present invention. According to the producing method of the present invention, the liquid introduced into the chamber forms a freeze-dried article, and thus a region of the support member covered in the liquid forms the embedded region in the freeze-dried structure of the present invention, and a region of the projecting member of the support member not covered in the liquid forms the protruding region in the freeze-dried structure of the present invention.

As described above, the support member may have a structure including the main body and the projecting member, wherein the main body and the projecting member are connected, and the projecting member projects outward from the main body, from an external face of the main body. In the support member, for example, the entirety or a part of the main body forms the embedded region in the freeze-dried structure, and the entirety or a part of the projecting member forms the protruding region in the freeze-dried structure.

The support member may be, for example, an integrally molded article of the main body and the projecting member, or in a form in which the main body and the projecting member are bonded.

In the support member, the external shape of the main body is not particularly limited, and may be, for example, the shape of a polyhedron, a cone, a cylinder, a sphere, or the like. Examples of the polyhedron include a cube and a cuboid Examples of the sphere include a perfect sphere and an ellipsoid.

In the support member, it is sufficient that the projecting member has, for example, a shape in which it protrudes outward from any face of the main body in a state of being connected with the main body. Accordingly, the projecting member may or may not have, for example, a projecting region that projects from any face of the projecting member, and, in the case of the latter, the projecting member may be, for example, a rod-like member, a plate-like member, or the like. The external shape of the projecting member is not particularly limited, and may be, for example, the shape of a prism, a pyramid, or the like. Examples of the prism include a polygonal prism and a cylinder, and examples of the pyramid include a polygonal pyramid and a cone.

The support member may be, for example, a non-porous material or a porous material, or may be constituted by both materials. In the support member, the main body may be, for example, a non-porous material or a porous material, and the projecting member may be, for example, a non-porous material or a porous material. Furthermore, the main body may be, for example, a frame structure constituted by a rod-like frame member. In this application, the frame structure is, for example, a type of the porous material.

The support member may be, for example, a non-woven fabric or a woven fabric, and the material thereof is not particularly limited. For example, specific examples thereof may be as described in the description of the freeze-dried structure of the present invention. The non woven fabric and the woven fabric are, for example, a type of the porous material Examples of the porous material include resin foams in addition to those described above.

The material of the support member is not particularly limited, and may be, for example, resin, paper, fiber, or the like, as described above, and, for example, specific examples thereof may be as described in the description of the description of the freeze-dried structure of the present invention.

The size of the support member is not particularly limited, and may be as described and exemplified in the description of the examples of the size in the freeze-dried structure of the present invention.

The type of liquid is not particularly limited, and may be, for example, a solvent such as an aqueous solvent. Furthermore, if the freeze-dried structure of the present invention is a food item, the liquid may be, for example, a broth, a soup, or a drink.

In the freeze-dried structure of the present invention, if the freeze-dried article contains a reagent, the liquid is, for example, a reagent solution containing the reagent. The reagent is, for example, a reagent for nucleic acid amplification. The type of nucleic acid amplification is not particularly limited, and is as described above. The reagent contained in the reagent solution may be constituted by, for example, one type of reagent component or two or more types of reagent components, but it is preferably a mixture of a plurality of reagent components for use in the nucleic acid amplification. The reagent is not particularly limited, and known reagents can be used according to the type of nucleic acid amplification, and may be as described in the description of the examples above.

The concentration of the reagent in the reagent solution is not particularly limited, and, for example, it can be set as appropriate such that the reagent for nucleic acid amplification in an amount for a single reaction is introduced into one chamber.

The reagent solution contains, for example, the reagent and the solvent. The solvent may be, for example, an aqueous solvent. The solvent is not particularly limited, and known solvents can be selected as appropriate according to the type of nucleic acid amplification and the type of reagent. Specific examples of the aqueous solvent include water and a buffer solution.

In the introducing, the type of chamber is not particularly limited, and it is sufficient that the chamber has a recess portion into which the liquid and the support member can be introduced. In the introducing, for example, one support member is introduced into one recess portion. The size of the recess portion can be set, for example, according to a target size of the freeze-dried structure.

In the introducing, the order in which the liquid and the support member are introduced into the chamber is not particularly limited, and the liquid may be introduced first or the support member may be introduced first, but the latter is preferable.

In the introducing, the support member is arranged such that a main body side thereof faces a bottom side of the chamber and a projecting member side thereof faces a side opposite to the bottom of the chamber.

As described above, the freeze-dried structure of the present invention is a structure in which a part of the support member is embedded in the freeze-dried article and a part of the support member protrudes outward from the freeze-dried article. Accordingly, in the introducing, it is possible to form the above-described structure through the following freeze drying treatment, by adjusting the degree to which the main body and the projecting member of the support member are covered in the liquid in the chamber. That is to say, it is sufficient that the liquid is introduced into the internal portion of the chamber until at least a part of the projecting member of the support member is exposed and the entirety or a part of the main body of the support member is covered.

Specific examples of the state in which the main body and the support member are covered in the liquid include the following three states.

That is to say, the first state is, for example, a state in which the entirety of the main body of the support member is covered in the liquid and the projecting member of the support member is not covered in the liquid. In this case, for example, in the support member, the freeze-dried article is formed on the entirety of the main body, and the freeze-dried article is not formed on the projecting member.

The second state is, for example, a state in which the entirety of the main body of the support member is covered in the liquid and a part of the projecting member of the support member is covered in the liquid. The "part of the projecting member of the support member" is, for example, a region of the projecting member on the side thereof connected to the main body. In this case, for example, in the support member, the freeze-dried article is formed on the entirety of the main body, and, furthermore, the freeze-dried article is also formed on the part of the projecting member, specifically, a part of the region of the projecting member on the side thereof connected to the main body.

The third state is, for example, a state in which only a part of the main body is covered in the liquid and the projecting member of the support member is not covered in the liquid. The "part of the main body" is, for example, a region of the main body on the side opposite to that connected to the projecting member. In this case, for example, in the support member, the freeze-dried article is formed on a part of the main body, specifically, a part of the region of the main body on the side opposite to that connected to the projecting member, and the freeze-dried article is not formed on the remaining region of the main body and the projecting member.

Next, in the freeze drying, freeze drying treatment is performed in the chamber into which the support member and the liquid have been introduced Thus, a freeze-dried structure in which the support member and a freeze-dried article of the liquid are included and the part of the projecting member of the support member protrudes from the freeze-dried article can be produced through the freeze drying treatment. In the freeze-dried structure, a region of the support member embedded in the freeze-dried article is the embedded region, and a region of the projecting member of the support member protruding outward from the freeze-dried article is the protruding region and is the holdable portion.

The condition for the freeze drying treatment is not particularly limited, and ordinary conditions can be used. The freeze drying treatment can be performed, for example, using an ordinary freeze drying apparatus. The freeze drying treatment includes, for example, freezing and drying. The freezing condition and the drying condition in the freeze drying treatment are not particularly limited, and it is sufficient that the conditions are for allowing the liquid to be frozen and allowing moisture to be removed from the frozen article that has been frozen.

The producing method of the present invention may further include, for example, taking out the freeze-dried structure from the internal portion of the chamber, after the freeze drying. In the taking out, for example, the freeze-dried structure is taken out from the internal portion of the chamber while a region of the freeze-dried structure protruding from the freeze-dried article is held. For example, a holding tool such as tweezers having a holding portion can be used for the holding. If the taken out freeze-dried structure is, for example, a reagent, the protruding region can be used as a holding portion also for introduction into a reaction vessel when used in reaction such as nucleic acid amplification and the following handling operations.

Hereinafter, the freeze-dried structure and the producing method thereof according to the present invention will be described by way of specific examples with reference to the drawings. In the drawings, the same constituent elements are denoted by the same reference numerals. The present invention is not limited to the following examples.

Embodiment 1

In this embodiment, an example will be described in which the main body of the support member is a frame structure.

FIG. 1 is a perspective view showing an example of a support member whose main body is a frame structure. A support member 10 has a main body 11 and a projecting member 12, and the main body 11 and the projecting member 12 are connected.

The main body 11 is a frame structure having a cubic external shape. That is to say, the cubic frame structure of the main body 11 is constituted by rod-like frame members 111, and regions 112 in the main body 11 defined by the frame members 111 are each a space.

The projecting member 12 may be, for example, a nonporous material or a porous material, and, in this embodiment, a nonporous material is shown as an example.

The projecting member 12 is a cylindrical member (a rod-like member with a circular cross-section). One of the end faces of the cylindrical member constituting the projecting member 12 is connected to the frame members 111 of the main body 11, at a portion near the center of a square face at an end of the cube constituting the main body 11. The method for connecting the projecting member 12 and the main body 11 is not particularly limited, and may be, for example, bonding or the like. Furthermore, the support member 10 may be, for example, an integrally molded article obtained by simultaneously molding the main body 11 and the projecting member 12.

The size of the support member 10 is not particularly limited, and, for example, it can be set as appropriate according to a target size of a freeze-dried structure that is to be produced.

Next, a producing method using the support member 10 will be described with reference to FIGS. 2A to 2D as an example FIGS. 2A to 2D are schematic views showing processes of the producing method.

Figure 2A:
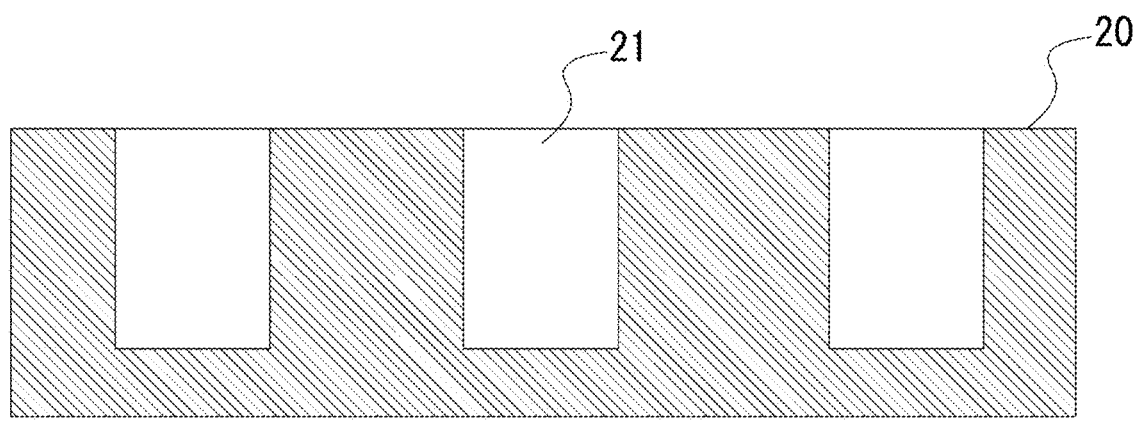
FIGS. 2A to 2D are schematic views showing producing processes of a freeze-dried structure in Embodiment 1, where

First, as shown in FIG. 2A, a freeze drying treatment vessel 20 having chambers 21 into each of which the support member 10 and the liquid are to be introduced is prepared. The size of each chamber 21 (alternatively referred to as a recess portion) in the vessel 20 is not particularly limited, and it can be set as appropriate according to a target size of the freeze-dried structure.

Figure 2B:
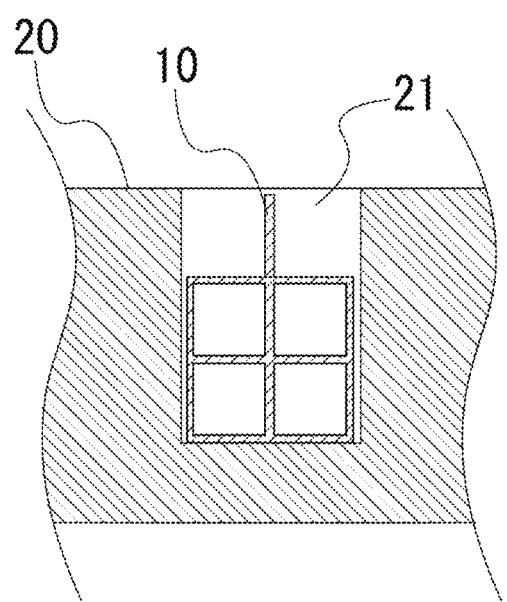

As shown in FIG. 2B, a support member 10 is introduced into the chamber 21 of the vessel 20. At this time, the support member 10 is introduced such that the main body 11 side of the support member 10 faces the bottom side of the chamber 21 and the projecting member 10 side of the support member 10 faces the upper side of the chamber 21.

Figure 2C:
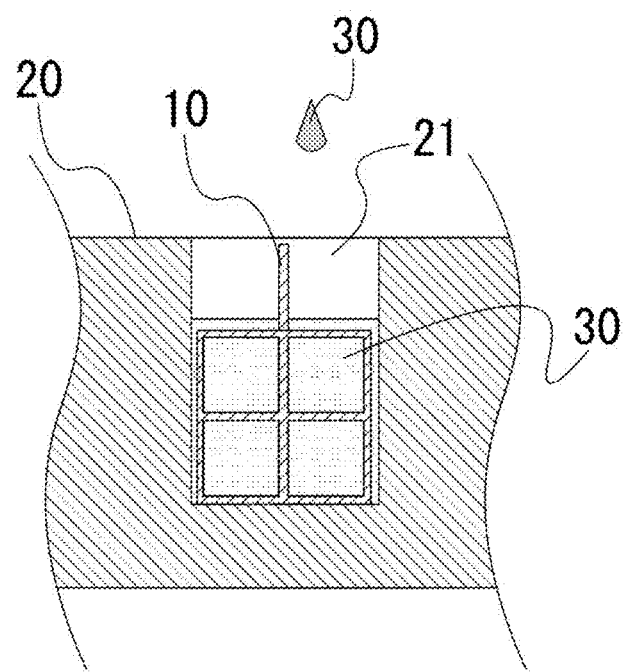

Next, as shown in FIG. 2C, a liquid 30 is introduced from the opening of the chamber 21. The liquid 30 is introduced until the main body 11 of the support member 10 is completely covered, and the projecting member 12 of the support member 10 is exposed from the liquid 30 (not covered in the liquid 30). Since the main body 11 of the support member 10 is a frame structure, the internal portion of the main body 11 is filled with the liquid 30.

Figure 2D:
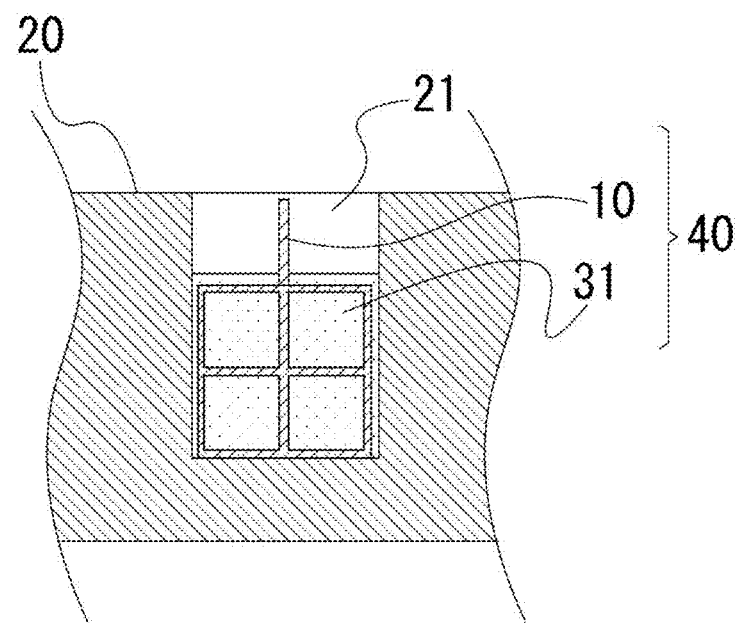

Then, freeze drying treatment is performed in the vessel 20 into which the support member 10 and the liquid 30 have been introduced. In this manner, as shown in FIG. 2D, a freeze-dried structure 40 containing a freeze-dried article 31 obtained by freeze drying the liquid 30 and the support member 10 is obtained in the chamber 21. In the freeze-dried structure 40, a region of the support member 10 embedded in the freeze-dried article 31 is the embedded region, and a region of the projecting member 12 of the support member 10 protruding outward from the freeze-dried article 31 is the protruding region.

If the exposed protruding region of the projecting member 12 of the support member 10 is used as a holdable portion and held by tweezers, the freeze-dried structure 40 in the chamber 21 can be easily taken out from the chamber 21. At this time, the tweezers are brought into contact only with the holdable portion of the freeze-dried structure 40, and do not come into contact with the freeze-dried article 31 of the freeze-dried structure 40, and thus it is possible to prevent the freeze-dried article 31 from being broken or chipped due to contact with tweezers during handling.

Furthermore, in the freeze-dried structure 40, if the freeze-dried article 31 contains a reagent, for example, a liquid (reagent solution) 30 is introduced into the chamber 21 such that, as described above, for example, the reagent in an amount for a single reaction (e.g., nucleic aid amplification reaction) is contained, and this reagent forms the freeze-dried article 31. Accordingly, in the case of performing handling while using the protruding region as a holdable portion and thereby preventing the freeze-dried article 31 from being broken or chipped, for example, it is passible to avoid a situation in which there is not enough of the reagent for a single reaction, and further avoid the usage of an excess amount of reagent to compensate for such a shortage.

Furthermore, in this embodiment, since the main body 11 of the support member 10 is the frame structure, the finally obtained freeze-dried structure 40 has a form in which the frame members 111 of the support member 10 extend throughout the internal portion of the freeze-dried article 31. Accordingly, for example, it is possible to improve the overall strength of the freeze-dried article 31, due to the structure of the main body 11 of the support member 10. Moreover, it is also possible to prevent the support member 10 from becoming detached from the freeze-dried article 31, even when the region protruding from the freeze-dried article 31 is held by tweezers and pulled upward in FIG. 2D.

Modified Example 1

Figure 3:
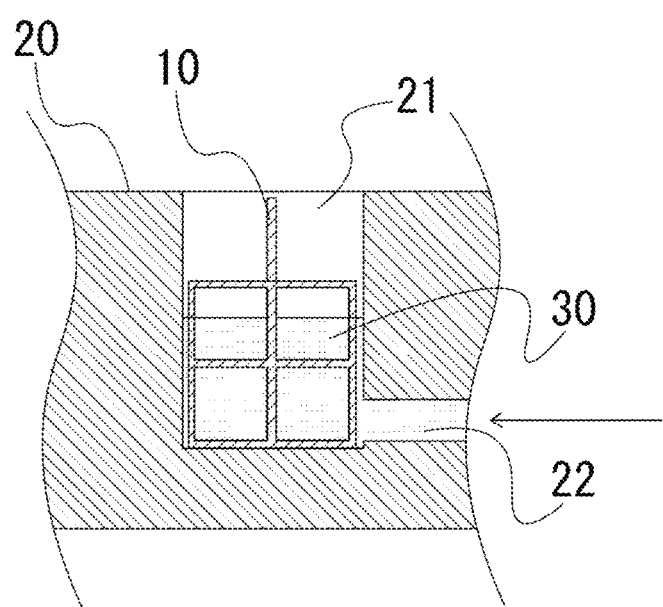
FIG. 3 is a cross-sectional view showing another example of a state in which the liquid is introduced into the chamber of the vessel into which the support member has been introduced.

For example, a method as shown in FIG. 3 can be given as an example of the method for introducing the liquid 30 into the chamber 21 of the vessel 20. That is to say, in FIG. 3, a side wall on the bottom side of the chamber 21 of the vessel 20 has a pipe 22 connected to the internal portion of the chamber 21. It is also possible to introduce the liquid 30 into the internal portion of the chamber 21 through the pipe 22.

Embodiment 2

In this embodiment, other examples of the support member whose main body is a frame structure will be described with reference to FIGS. 4 and 5.

Figure 4:
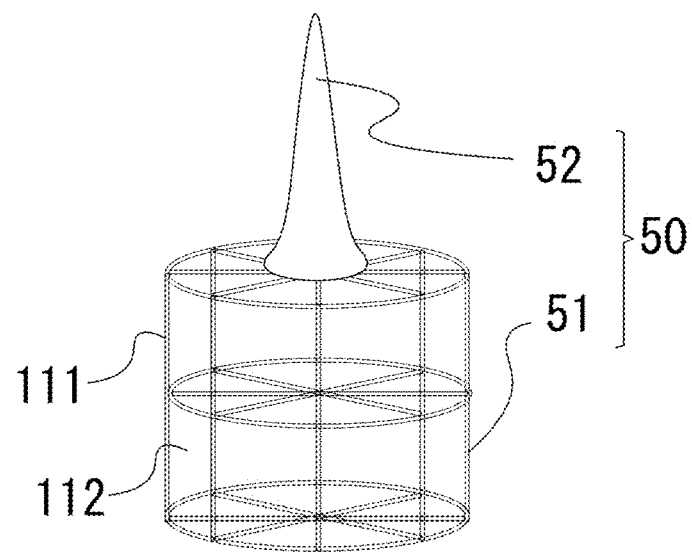
FIG. 4 is a perspective view schematically showing a support member in Embodiment 2.

FIG. 4 is a perspective view showing an example of a support member whose main body has a cylindrical external shape. A support member 50 has a main body 51 and a projecting member 52, and the main body 51 and the projecting member 52 are connected.

The main body 51 is a frame structure having a cylindrical external shape. That is to say, the cylindrical frame structure of the main body 51 is constituted by rod-like frame members 111, and regions 112 in the main body 51 defined by the frame members 111 are each a space. Eight frame members 111 are arranged extending in the upper-lower direction on the side face of the main body 51. Furthermore, eight frame members 111 are arranged extending from the center toward the circumference on each of the upper and lower faces of the main body 51, and are connected to the upper and lower ends of the frame members 111 on the circumference.

The projecting member 52 may be, for example, a nonporous material or a porous material, and, in this embodiment, a nonporous material is shown as an example.

The projecting member 52 is a substantially conical member (substantially conical rod like member). The bottom face of the substantially conical member constituting the projecting member 52 is connected to the frame members 111 of the main body 51, at a portion near the center of a circular face at an end of the cylindrical member constituting the main body 51.

The producing method using the support member 50 is not particularly limited, that is, the method may be as described in the description of Embodiment 1 above, and the effects thereof may be as described in the description of Embodiment 1 above Since the main body 51 of the support member 50 has a cylindrical external shape, for example, it is also possible that the internal structure (recess portion) of the chamber is a void having a cylindrical shape as well.

Figure 5:
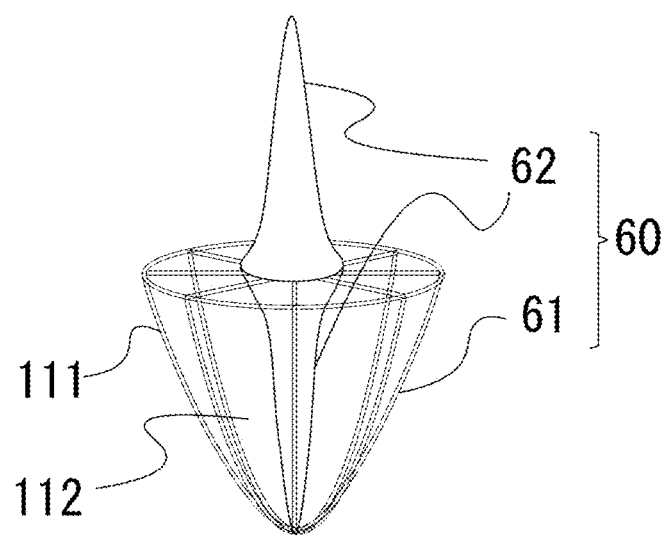
FIG. 5 is a perspective view schematically showing a support member in Embodiment 2.

FIG. 5 is a perspective view showing an example of a support member whose main body has a substantially conical external shape. A support member 60 has a main body 61 and a projecting member 62, and the main body 61 and the projecting member 62 are connected.

The main body 61 has a frame structure having a substantially conical external shape. That is to say, the substantially conical frame structure of the main body 61 is constituted by rod-like frame members 111, and regions 112 in the main body 61 defined by the frame members 111 are each a space.

The projecting member 62 is a rod-like member, and has a shape whose cross-sectional area at a portion close to the middle in the axial direction is relatively large and becomes smaller toward the two ends. It can be said that the projecting member 62 has, for example, a shape in which two substantially conical members are connected at their bottom faces. An end (a lower end portion in FIG. 5) and a circumference near the middle in the axial direction of the projecting member 62 are connected to the frame member of the main body 61. Specifically, eight frame members 111 are arranged extending from the center of the projecting member 62 toward the circumference, at a portion near the middle of the projecting member 62, frame members 111 are further arranged so as to extend toward the lower side of the projecting member 62 from the ends of the frame members, and the eight frame members 111 are connected at the lower end of the projecting member 62.

Figure 6:
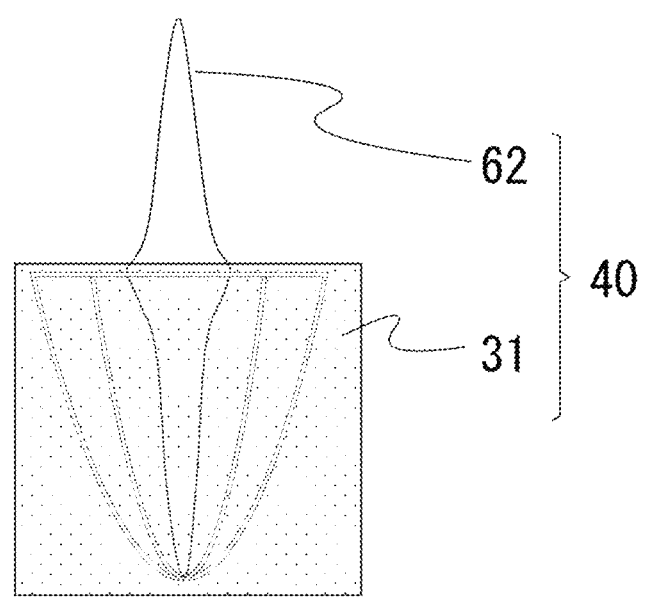
FIG. 6 is a side view schematically showing a freeze-dried structure produced using the support member of Embodiment 2 shown in FIG. 5.

The producing method using the support member 60 is not particularly limited, that is, the method may be as described in the description of Embodiment 1 above, and the effects thereof may be as described in the description of Embodiment 1 above. As in Embodiment 1 above, if the internal structure (recess portion) of the chamber is in the shape of a cuboid, the freeze-dried structure 40 as shown in FIG. 6 can be produced, for example, using a producing method using the support member 60. FIG. 6 is a plan view schematically showing the freeze-dried structure.

Embodiment 3

In this embodiment, an example of the support member whose main body is a non porous material will be described with reference to FIG. 7.

Figure 7:
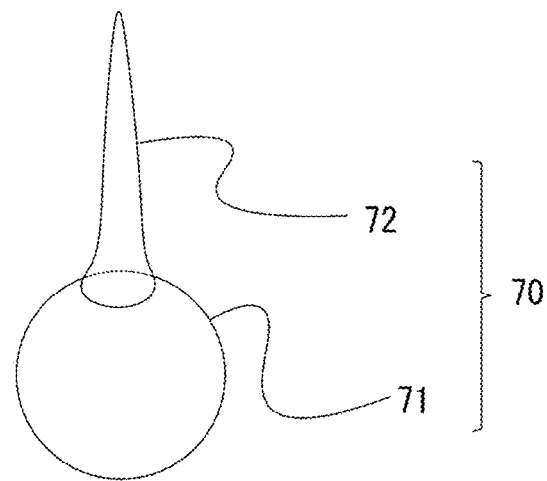
FIG. 7 is a perspective view schematically showing a support member in Embodiment 3.

FIG. 7 is a perspective view showing an example of a support member whose main body is a spherical member and whose projecting member is a substantially conical member. A support member 70 has a main body 71 and a projecting member 72, and the main body 71 and the projecting member 72 are connected. Specifically, y, the bottom face of the substantially conical member constituting the projecting member 72 is connected to the surface of the spherical member constituting the main body 51.

The projecting member 72 may be a non-porous material or a porous material, and, in this embodiment, a non-porous material is shown as an example.

The producing method using the support member 70 is not particularly limited, that is, the method may be as described in the description of Embodiment 1 above, and the effects thereof may be as described in the description of Embodiment 1 above.

If the support member 70 of this embodiment is used, the finally obtained freeze-dried structure has a form in which the main body 71 is embedded in the internal portion of the freeze-dried article. Since the main body 71 of the support member 70 is a spherical member, for example, it is possible to prevent the support member 70 from becoming detached from the freeze-dried article, even when the freeze-dried structure is pulled upward toward the upper end of the support member 70 while the protruding region of the projecting member 72 protruding from the freeze-dried article is held by tweezers.

Embodiment 4

In this embodiment, an example of the support member whose main body is a porous material will be described with reference to FIG. 8.

Figure 8:
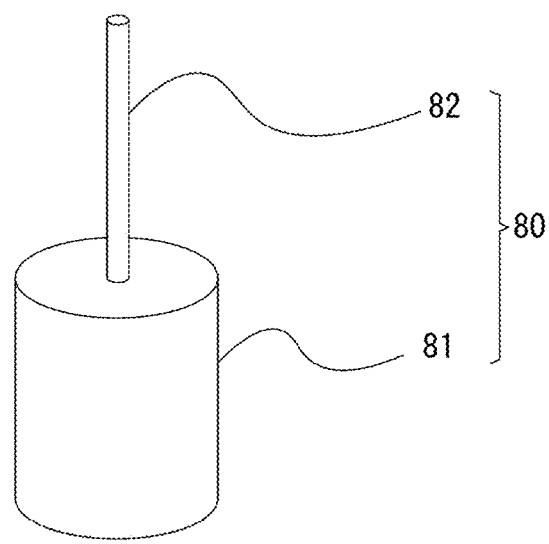
FIG. 8 is a perspective view schematically showing a support member in Embodiment 4.

FIG. 8 is a perspective view showing an example of a support member whose main body is a cylindrical member and whose projecting member is a thin rod-like member (cylindrical member). A support member 80 has a main body 81 and a projecting member 82, and the main body 81 and the projecting member 82 are connected. Specifically, the bottom face of the rod-like member constituting the projecting member 82 is connected to the surface of the cylindrical member constituting the main body 81.

The projecting member 82 may be a non-porous material or a porous material, and, in this embodiment, a non-porous material is shown as an example.

In the case of producing a freeze-dried structure for nucleic acid amplification as with Embodiment 1 above, for example, the following conditions may be given as an example of the size of the support member 80. Furthermore, in the case of producing the freeze-dried structure using the support member 80, for example, the following conditions may be given as an example of the size of the internal space of the chamber and the amount of liquid introduced into one chamber.

Support Member 80
   Overall size height: 20 mm, width: 5 mm, depth: 5 mm
Main Body 81
   Material: PP
   Size: φ5 mm
Projecting Member 82
   Material: PP
   Size of projecting member 81 height: 15 mm, diameter: (φ2 mm
Ratio Between Heights of Main Body 81 and Projecting Member 82
   Main body 81:projecting member 82=1:3
Internal Space of Chamber
   Width: 5 mm, depth: 5 mm, height: 20 mm
Reagent Solution
   Amount: 20 μL The producing method using the support member 80 is not particularly limited, that is, the method may be as described in the description of Embodiment 1 above, and the effects thereof may be as described in the description of Embodiment 1 above.

Since the main body 81 of the support member 80 in this embodiment is a porous material, for example, as with the main body constituted by the frame structure in Embodiment 1, the liquid enters voids of the main body 81 as well, and thus a freeze-dried article is formed so as to be joined throughout portions on the outer side of the main body 81 and in the voids of the main body 81. Accordingly, for example, it is possible to improve the overall strength of the freeze-dried article, due to the structure of the main body 81 of the support member 80. Moreover, it is also possible to prevent the support member 80 from becoming detached from the freeze-dried article, even when the protruding region of the projecting member 82 protruding from the freeze-dried article is held by tweezers and pulled upward in FIG. 8.

Embodiment 5

When a freeze-dried reagent is used for a nucleic acid amplification reaction, typically, the freeze-dried reagent and a liquid (e.g., a liquid sample and optionally an aqueous solvent) are added to a reaction vessel, and the reagent in the freeze-dried reagent is dissolved in the liquid, after which a nucleic aid amplification reaction is caused to occur. However, in the case in which only an ordinary freeze-dried reagent, that is, a freeze-dried article obtained by merely freeze drying a reagent solution, is used, for example, the freeze-dried article may float on the introduced liquid or may become trapped in a pocket-like space inside the reaction vessel when the freeze-dried article is introduced into the reaction vessel. In such a case, for example, although the freeze-dried reagent contains a reagent in an amount necessary for a single nucleic acid amplification reaction, the necessary amount of reagent may not be dissolved in the liquid. However, the freeze-dried structure of the present invention can be first introduced into the reaction vessel while the protruding region (the holdable portion) is held by tweezers as described above, and thus, for example, the freeze-dried article can be arranged inside the reaction vessel such that the freeze-dried article formed on the main body side of the support member is positioned on the bottom of the reaction vessel. Furthermore, the liquid that is introduced into the reaction vessel accumulates from the bottom of the reaction vessel, and thus it is possible to efficiently bring the dried article into contact with the liquid, and to sufficiently dissolve the reagent contained in the freeze-dried article in the liquid.

Furthermore, the above-described floating of the freeze-dried article can be more effectively prevented, for example, by adjusting the length in the axial direction of the support member in the freeze-dried structure as described below.

Typically, after the reagent and the liquid are introduced into the reaction vessel, a cover is attached thereto so as to cover the opening, and a reaction is caused to occur. Thus, the overall length in the axial direction (e.g., the axial direction of the projecting member in the support member) of the freeze-dried structure is preferably set according to the height of the reaction vessel in the state in which the cover is attached to the reaction vessel (e.g., the length from the bottom face of the internal portion of the reaction vessel to the ceiling face of the internal portion of the cover) and the depth of the liquid introduced into the reaction vessel. Note that the internal portion of the reaction vessel preferably has, for example, a shape that is elongated in the vertical direction (height direction). Furthermore, the overall length of the freeze-dried structure is preferably greater than the maximum width in the bottom face direction of the reaction vessel. With this setting, for example, even when the freeze-dried article in the freeze-dried structure is likely to float in the liquid introduced into the reaction vessel, the support member in the freeze-dried structure comes into contact with the ceiling face of the cover in the reaction vessel, functions as a prop, and can keep the freeze-dried article in the liquid.

In the description above, the invention of the present application was described by way of embodiments, but the invention of the present application is not limited to the foregoing embodiments. Various changes that can be understood by those skilled in the art can be made to the configuration and details of the invention of the present application within the scope of the invention of the present application.

According to the freeze-dried structure of the present invention, the protruding region of the support member protrudes outward from the freeze-dried article. Accordingly, it is possible to hold the protruding region of the freeze-dried structure using a holding tool such as tweezers, without holding the surface of the freeze-dried article. Thus, it is possible to perform handling while reducing damage to a brittle freeze-dried article in the freeze-dried structure.

LIST OF REFERENCE NUMERALS 10, 50, 60, 70, 80 Support member
11, 51, 61, 71, 81 Main body
12, 52, 62, 72, 82 Projecting member
111 Frame member
112 Region
20 Vessel
21 Chamber
22 Pipe
30 liquid
31 Freeze-dried article
40 Freeze-dried structure

What is claimed is:

1. A method for producing a freeze-dried structure, comprising:
   introducing a support member and a liquid into an internal portion of a chamber; and
   performing freeze drying treatment in the chamber, wherein
   the support member has a main body and a projecting member,
   the main body and the projecting member are connected,
   in the support member, the projecting member projects outward from the main body, from an external face of the main body,
   in the introducing,
      the support member is arranged such that a main body side thereof faces a bottom side of the chamber and a projecting member side thereof faces a side opposite to the bottom side of the chamber, and
      the liquid is introduced into the internal portion of the chamber until at least a part of the projecting member of the support member is exposed and an entirety or a part of the main body of the support member is covered, and
   in the freeze drying,
      a freeze-dried structure in which the support member and a freeze-dried article of the liquid are included and the part of the projecting member of the support member protrudes from the freeze-dried article is produced through the freeze drying treatment.

2. The producing method according to claim 1, wherein the support member is a non-porous material.

3. The producing method according to claim 1, wherein the support member is a porous material.

4. The producing method according to claim 1, wherein the support member is made of resin, paper, or fiber.

5. The producing method according to claim 1, wherein the support member is a non-woven fabric or woven fabric.

6. The producing method according to claim 1, wherein the main body of the support member has an external shape of a polyhedron, a cone, a cylinder, or a sphere.

7. The producing method according to claim 1, further comprising taking out the freeze-dried structure from the internal portion of the chamber, after the freeze drying,
   wherein, in the taking out, the freeze-dried structure is taken out from the internal portion of the chamber while a region of the freeze-dried structure protruding from the freeze-dried article is held.

* * * * *